United States Patent
Lipton et al.

(10) Patent No.: US 7,232,804 B2
(45) Date of Patent: Jun. 19, 2007

(54) USE OF KPV TRIPEPTIDE FOR DERMATOLOGICAL DISORDERS

(75) Inventors: James M. Lipton, Woodland Hills, CA (US); Anna P. Catania, Milan (IT)

(73) Assignee: Zengen, Inc., Canoga Park, CA (US)

( * ) Notice: Subject to any disclaimer, the term of this patent is extended or adjusted under 35 U.S.C. 154(b) by 82 days.

(21) Appl. No.: 11/049,063

(22) Filed: Feb. 2, 2005

(65) Prior Publication Data

US 2005/0124551 A1    Jun. 9, 2005

Related U.S. Application Data

(62) Division of application No. 09/828,272, filed on Apr. 6, 2001, now Pat. No. 6,894,028.

(51) Int. Cl.
*A61K 38/00*    (2006.01)

(52) U.S. Cl. ............................................. 514/18; 514/2

(58) Field of Classification Search ..................... None
See application file for complete search history.

(56) References Cited

OTHER PUBLICATIONS

Ichiyama et al. 2000, Ann. N.Y. Acad. Sci., vol. 917, pp. 221-226.*
Saunders et al., 2001, J. Biol. Chem., vol. 276, No. 22, pp. 18897-18904.*
The Merk Manual, 16th Edition, 1992, pp. 2407-2409.*
Stedman, T.L. 2000. Stedman's Medical Dictionary. Lippincott Williams & Wilkins, Philadelphia. xxxvi, 2098 pp. 897-898.

* cited by examiner

*Primary Examiner*—B. Dell Chism
(74) *Attorney, Agent, or Firm*—Gregory M. Zinkl; Dykema Gossett PLLC

(57) ABSTRACT

The present invention is directed to a prevention and treatment for dermatological disorders. One aspect of this invention involves a dermatological treatment comprising one or more polypeptides with an amino acid sequence including KPV (SEQ. ID. NO. 1), MEHFRWGKPV (SEQ. ID. NO. 2), HFRWGKPV (SEQ. ID. NO. 3), or SYSMEHFRWGKPV (SEQ. ID. NO. 4) for the treatment and prevention of dermatological disorders. The polypeptides are at a level to effectively treat the cutaneous inflammation and are carried by a carrier. The one or more polypeptides can also be a dimer formed from any of the amino acid sequence above.

16 Claims, 1 Drawing Sheet

SEQUENCE LISTING

```
<160> NUMBER OF SEQ ID NOS: 7

<210> SEQ ID NO 1
<211> LENGTH: 3
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 1

Lys Pro Val
1

<210> SEQ ID NO 2
<211> LENGTH: 10
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 2

Met Glu His Phe Arg Trp Gly Lys Pro Val
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 3

His Phe Arg Trp Gly Lys Pro Val
1               5

<210> SEQ ID NO 4
<211> LENGTH: 13
<212> TYPE: PRT
<213> ORGANISM: Artificial Sequence
<220> FEATURE:
<223> OTHER INFORMATION: alpha-MSH with anti-inflammatory,
      anti-bacterial, anti-fungal and antipyretic properties.

<400> SEQUENCE: 4

Ser Tyr Ser Met Glu His Phe Arg Trp Gly Lys Pro Val
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 5

Gly Lys Pro Val
1

<210> SEQ ID NO 6
<211> LENGTH: 5
<212> TYPE: PRT
<213> ORGANISM: Artificial Sequence
```

```
-continued

<220> FEATURE:
<223> OTHER INFORMATION: Designed polypeptide with anti-inflammatory,
      anti-bacterial, anti-fungal and antipyretic properties.

<400> SEQUENCE: 6

Trp Gly Pro Lys Val
1               5

<210> SEQ ID NO 7
<211> LENGTH: 6
<212> TYPE: PRT
<213> ORGANISM: Artificial Sequence
<220> FEATURE:
<223> OTHER INFORMATION: Designed polypeptide with anti-inflammatory,
      anti-bacterial, anti-fungal and antipyretic properties.

<400> SEQUENCE: 7

Arg Trp Gly Lys Pro Val
1               5
```

USE OF KPV TRIPEPTIDE FOR DERMATOLOGICAL DISORDERS

RELATED APPLICATIONS

This application is a Divisional of U.S. application Ser. No. 09/828,272 filed on Apr. 6, 2001, now U.S. Pat. No. 6,894,028 and which is incorporated by reference as if fully set forth herein, including figures and tables.

FIELD OF INVENTION

The present invention relates to a method of treating dermatological disorders with formulations including a polypeptide having a KPV amino acid sequence.

BACKGROUND OF INVENTION

The skin, also known as the integumentary system, is the largest organ in the body. The skin is an organ with its own anatomy, physiology, and functions. For example, some of the integumentary system's functions are as a protection from the environment and microorganisms, as a sensory system, as a temperature control system, as an excretory system, and even as a chemical factory in the production of vitamin D. Unfortunately, as with any organ that has its own anatomy and physiology, comes pathology.

There are over 2000 disorders that can affect the integumentary system. Fitzpatrick, Polono, Suurmound, *Color Atlas and Synopsis of Clinical Dermatology* (1983). What separates the disorders of the integumentary system from other organs is that the symptoms of the disorders of the integumentary system are so readily sensed and palpable to the one afflicted and visible to that person and others. Additionally, the manifestations and symptoms of skin disorders are easily and immediately exacerbated by the sufferer of the disorder. For example, many of the 2000 disorders of the skin manifest with lesions that carry with them the symptoms of pruritus ("itching"), erythema (heat and redness), and algesia (pain). A person trying to relieve the symptom of a skin disorder may make the condition worse by consciously or, even more commonly, unconsciously scratching at lesions manifested by the disorder. These differences, as well as many others, make the treatment of skin ailments a unique and difficult problem.

Some of the more common and well-recognized diseases are the psoriatic disorders and the specific abnormalities that fall within the class of eczematous dermatitis. Psoriasis, for example, affects about three percent of the world's population. See, Baker, Burton, Zieve, *Principles of Ambulatory Medicine*, Williams and Wilkins (1982).

The psoriatic syndromes are related by a constellation of symptoms including pruritis, pain, visible lesions, inflammation, hair and nail changes and, in up to 32% of the cases, debilitating arthritis. The skin lesions can be distributed as single lesions or lesions localized to one area, or may be regional and generalized in a universal pattern affecting the integument as well as the skin appendages (hair and nails). The presentation is rarely symmetrical and favors areas of friction.

The pathophysiology of the syndromes includes a marked decrease in epidermal turnover time resulting in a markedly increased number of mitotic cells in the dividing pool. This creates a vastly increased epidermal proliferation. The epidermis and the dermis appear to respond as an integrated unit and show primary changes in the keratinocytes and keratogenous zones of the epidermis and inflammatory changes in the dermis. The resulting lesions are located in an area of erythroderma and include papules and plaques with marked silvery-white scaling. The papules may become pustules upon contamination. See, Fitzpatrick, et al. *Color Atlas and Synopsis of Clinical Dermatology* McGraw Hill Book Co. (1983); Barker, Burton Zieve, *Principles of Ambulatory Medicine*, Williams & Wilkins, (1982).

Treatment for sufferers of psoriatic syndromes has been difficult. Treatment decisions are made considering the type of psoriasis, the stage of the disease, the site of involvement, the age of the patient and the degree of disability or disfigurement. It is well known that many treatments available must be curtailed or even removed from consideration depending on the factors mentioned above. For example, methotrexate, a highly toxic anti-metabolite and cytotoxic medicine, which is used in recalcitrant psoriasis, can be fatal to patients. Other methods of treatment are time consuming, expensive, show poor patient compliance and are poorly tolerated by many patients. These include, but are not limited to, Psorelen Long Wave Ultra Violet Light, Retinoid therapy, Tar, and intralesional injections of steroids (which are quite painful). In cases with secondary fungal infection, ketoconazole (Nizoral®), a very common and popular antifungal, is used. Ketoconazole, however, has serious side effects which may be fatal when combined with terfenadine; known by the public as Seldane® (a commonly used allergy medication).

Avoidance of these complications presents a welcome invitation to a new preparation that is well tolerated by a number of people suffering from psoriasis. As will be described below, α-MSH and/or its derivatives show efficacy in these areas.

Another area of dermatological abnormalities that show a positive response to α-MSH and/or its derivatives are the delayed hypersensitivity reactions, i.e. allergic contact dermatitis (an example would be a reaction from an exposure to poison ivy) and primary irritant contact dermatitis (an example would be a reaction from repeated exposure to certain substances to which a person may be hypersensitive).

Similar to psoriasis, and most of the dermatological disorders, contact dermatitis shows a constellation of integumentary changes. Among these are irregular and poorly outlined patches of erythema and edema, vesicles, erosions exuding serum, and crusts. In chronic forms of contact dermatitis, a person may suffer patches of lichenification (thickening of the epidermis with deepening of the skin lines in parallel or rhomboidal pattern), hyperpigmentation and scaring from excoriation.

Early and tolerated treatment is of a great benefit to people suffering from contact dermatitis. Unfortunately, the standby treatment is, again, antihistamines and steroids; oral and topical, i.e. oral in the acute phase and topical in the subacute and chronic phase. Although the steroids function well in reduction of symptoms, they share the same drawbacks as listed above. Additionally, steroids would not be used in a prophylactic way due to their list of adverse side effects. A medication is needed that survives both as a symptomatic treatment as well as a preventative one. This medication would have applications in many of the diseases listed as well as others with just as complicated nomenclature and pathophysiology.

Regardless of the difficult nomenclature, however, many diseases of the integumentary system share the same pathophysiology and, therefore, share similar symptoms and sequelae. Of these symptoms, inflammation, algisia and pruritis are the most common, and it is these symptoms to which physicians direct their attention in the empirical treatment of skin disease. As with the diseases mentioned above, the overwhelming first line of treatment for physicians treating skin disease, especially non-specialists in the area, is some preparation of a steroid-based medicine. Hydrocortisone, betamethasone and prednisolone are commonly used steroids in many prescription and over-the-counter preparations of anti-inflammatory and anti-pruritic topical preparations. Often a physician will use an antihistamine in addition to, or as an alternative for, steroid therapy to control the effects of vascular permeability that is the result of the release of histamine from mast cells in the primary stages of inflammation. See, Ryan and Majano, *Inflammation*, a Scope Publication, The Upjohn Company, (1977).

Although the use of topical steroids and antihistamines are useful, they carry with them a long history of well-established and unwanted side effects. For example, antihistamines cause drowsiness and can be poorly tolerated in many individuals. Topical steroids are known to create problems for the integument that may be worse than the lesion they were intended to ameliorate. Here, the treatment may be worse than the disease.

For example, topical steroid use for as little as two weeks can cause: 1) telangiectasia (dilation of capillaries and sometimes of terminal arteries producing an angioma of macular appearance, or hyperemic spot) which, can be quite unsightly; 2) skin atrophy or thinning of the skin; and 3), mask an infection or suppress the host response to invasion by opportunistic pathogens.

This latter point is of great importance in any dermatological disorder that may result in an open lesion. Open lesions are a notoriously favorable environment for opportunistic infection. The warmth, blood supply, pH, and necrotic tissue are all conducive to bacterial or fungal colonization. Using a steroid in this environment may slow the response to an infection and thereby mask commonly observed and treated signs and symptoms of an infection; namely, purulence or puss. Thus, a simple infection in the presence of a topical steroid can be masked to the point of serious infection or even sepsis.

Reduced killing of pathogens is a detrimental consequence of therapy with anti-infammatory drugs. In addition to α MSH's and/or its derivatives potent anti-inflammatory effects, a MSH and/or its derivatives shows anti-microbial efficacy as well. It has been shown that the influences of αMSH and/or its derivatives on common skin pathogens, i.e. *Staphylococcus Aureus* and *Candida Albicans*, showed bactericidal and fungicidal properties. See, Cutull, Cristiani, Lipton and Catania, *Antimicrobial Effects of α MSH Peptides*, Journal of Leukocyte Biology, Volume 67, February 2000.

It follows that the use of a preparation that could offer all the benefits of steroid preparations, antipyretics, analgesics, and antihistamines but without the attendant side effects, will be a great addition to the available avenues of treatment of these types of symptoms and these types of disorders.

SUMMARY OF THE INVENTION

The present invention is directed to a treatment for dermatological disorders and a method for preventing dermatological disorders and their associated symptomatolgy. One aspect of this invention involves a dermatological treatment comprising one or more polypeptides with an amino acid sequence including KPV (SEQ. ID. NO. 1), MEHFRWGKPV (SEQ. ID. NO. 2), HFRWGKPV (SEQ. ID. NO. 3), or SYSMEHFRWGKPV (SEQ. ID. NO. 4) for the treatment of the cutaneous sequelae associated with dermatological disorders. The polypeptides are at a level to effectively treat the cutaneous inflammation, edema, erythema, opportunistic infection and pruritis, and are dissolved into a carrier.

The one or more polypeptides can also be a dimer formed from any of the amino acid sequences above. In one preferred embodiment of the invention, the one or more polypeptides are dissolved in an appropriate carrier and are used to cure or ameliorate the sequelae of dermatological disorders. In another preferred embodiment, the carrier has its own medicinal and/or palliative properties. In another preferred embodiment of the invention, the one or more polypeptides are dissolved in a liquid that is associated with an absorbent material for application on the skin.

GENERAL DESCRIPTION OF THE INVENTION

Figure 1:
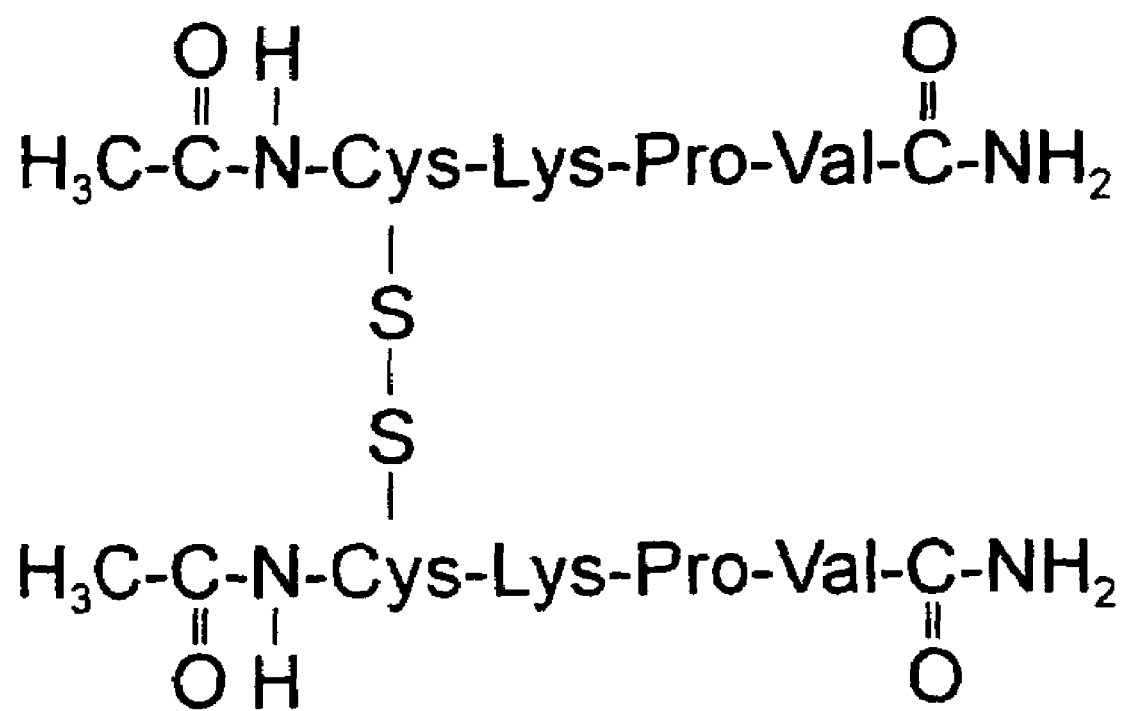
FIG. 1 shows a representation of the chemical structure of one form of the KPV dimer for use with one aspect of the invention.

The references cited above and below are incorporated by reference as if fully set forth herein. The present invention involves a treatment for curing dermatological disorders, methods of treatment of the sequelae of dermatological disorders when they have manifested, and prevention of outbreaks or manifestations in dermatological disorders with the use of alpha-melanocyte stimulating hormone ("α-MSH") and/or its derivatives.

α-MSH is an ancient thirteen amino-acid peptide (SEQ. ID. NO. 4) produced by post-translational processing of the larger precursor molecule propiomelanocortin. It shares the 1-13 amino acid sequen ce with adrenocorticotropic hormone ("ACTH"), also derived from propiomelanocortin. α-MSH is known to be secreted by many cell types including pituitary cells, monocytes, melanocytes, and keratinocytes. It can be found in the human epidermis, the skin of rats or in the mucosal barrier of the gastrointestinal tract in intact and hypophysectomized rats. See e.g. Eberlie, A. N., *The Melanotrophins*, Karger, Basel, Switzerland (1998); Lipton, J. M., et al., *Anti-inflammatory Influence of the Neuroimmunomodulator α-MSH, Immunol. Today* 18, 140-145 (1997); Thody, A. J., et al., *MSH Peptides are Present in Mammalian Skin, Peptides* 4, 813-815 (1983); Fox, J. A., et al., *Immunoreactive α-Melanocyte Stimulating Hormone, Its Distribution in the Gastrointestinal Tract of Intact and Hypophysectomized Rats, Life. Sci.* 18, 2127-2132 (1981).

α-MSH and/or its derivatives are known to have potent antipyretic, anti-inflammatory properties and antifungal and antibiotic effects; yet they have extremely low toxicity. They can reduce production of host cells' proinflammatory mediators in vitro, and can also reduce production of local and systemic reactions in animal models for inflammation. The "core" α-MSH sequence (4-10) (SEQ. ID. NO. 2), for example, has learning and memory behavioral effects but little antipyretic and anti-inflammatory activity. In contrast, the active message sequence for the antipyretic and anti-inflammatory activities resides in the C-terminal amino-acid sequence of α-MSH, that is, lysine-proline-valine ("Lys-Pro-Val" or "KPV") (SEQ. ID. NO. 1). This tripeptide has activities in vitro and in vivo that parallel those of the parent molecule.

The anti-inflammatory activity of α-MSH and/or its derivatives is disclosed in the following patents which are hereby incorporated by reference: U.S. Pat. No. 5,028,592, issued on Jul. 2, 1991 to Lipton, J. M., entitled Antipyretic and Anti-inflammatory Lys-Pro-Val Compositions and Method of Use; U.S. Pat. No. 5,157,023, issued on Oct. 20, 1992 to Lipton, J. M., entitled Antipyretic and Anti-inflammatory Lys-Pro-Val Compositions and Method of Use; see also Catania, A., et al., α-*Melanocyte Stimulating Hormone in the Modulation of Host Reactions, Endocr. Rev.* 14, 564-576 (1993); Lipton, J. M., et al., *Anti-inflammatory Influence of the Neuroimmunomodulator of α-MSH, Immunol. Today* 18, 140-145 (1997); Rajora, N., et al., α-*MSH Production Receptors and Influence on Neopterin, in a Human Monocyte/macrophage Cell Line, J. Leukoc. Biol.* 59, 248-253 (1996); Star; R. A., et. al., *Evidence of Autocrine Modulation of Macrophage Nitric Oxide Synthase by α-MSH, Proc. Nat'l. Acad. Sci.* (*USA*) 92, 8015-8020 (1995); Lipton, J. M., et al., *Anti-inflammatory Effects of the Neuropeptide α-MSH in Acute Chronic and Systemic inflammation, Ann. N.Y. Acad. Sci.* 741, 137-148 (1994); Fajora, N., et al., α-*MSH Modulates Local and Circulating Tumor Necrosis Factor α in Experimental Brain Inflammation, J. Neuroosci,* 17, 2181-2186 (1995); Richards, D. B., et al., Effect of α-*MSH* (11-13) (*lysine-proline-valine*) *on Fever in the Rabbit, Peptides* 5, 815-817 (1984); Hiltz, M. E., et al., *Anti-inflammatory Activity of a COOH-terminal Fragment of the Neuropeptide α-MSH, FASEB J.* 3, 2282-2284 (1989).

In a preferred embodiment of the invention, these anti-inflammatory activities are most particularly associated with the C-terminal amino-acid sequence—KPV. This tripeptide, along with □-MSH and/or its derivatives, are effective over a very broad range of concentrations, including picomolar concentrations that normally occur in human plasma.

As discussed in the background section, a topical treatment for dermatological disorders is desired. For treatment of these conditions, α-MSH and/or its derivatives can be applied to the affected areas by methods known in the art. For example, α-MSH and/or its derivatives can be dissolved in solutions such as a phosphate buffer saline, hyalurinate, methylcellulose, carboxymethlcellulose, or ethanol. Common carriers such as cream, ointment, balm, aerosol foam, aerosol spray, pump spray, gel, stick, liquid, or absorbent material can carry α-MSH and/or its derivatives as active ingredients for treating dermatological disorders. These carriers can be applied to the affected portion of the integument by spray, absorbent material wipes, swabs or any of a number of applicators known in the art, bandages, or fingers.

More specifically, one preferred embodiment of the invention is to dissolve α-MSH and/or its derivatives in an ointment, cream, lotion, balm, aerosol foam, aerosol spray, pump spray, gel, stick, or liquid carrier. The carrier containing the solvated α-MSH and/or its derivatives may have palliative properties in and of themselves, i.e. lanolin an emollient or white petroleum as a moisturizing agent. Additionally, the α-MSH and/or its derivatives can be combined with a carrier and another chemical with medicinal properties of its own, i.e. hydrocortisone cream. The resulting combination can be topically applied to the skin.

Another preferred embodiment of the invention is a treatment packet with a wipe made of absorbent material that is treated with α-MSH and/or its derivatives that have been dissolved into a liquid-based carrier. The process for making wipes of absorbent material is well known in the art. For example, baby wipes, moist towelettes, make-up removal cloths, and alcohol swabs are all wipes of absorbent material. Commercial examples of such wipes include CHUBS® Baby Soft Wipes, DEXUS® Antibacterial Hand Wipes, DEXUS® Makeup Remover Wipes, TINACTIN® Sports Wipes for Athlete's Foot, and B-D® Alcohol Swabs. Treatment of the wipe's absorbent material is accomplished by first soaking the absorbent material in a solution of α-MSH and/or its derivatives. The wipe remains in a liquid-impermeable packaging until use, when the package is opened and the wet wipe is applied to the affected portion of the integument. The processes for making liquid-impermeable packages are well known in the art. For example, packages made of layers of paper, metal foil, and metal foil coated paper are commonly used for packaging wipes of absorbent material. For example, moist towelettes, such as MASSENGILL® Feminine Cleansing Soft Cloth Towelettes, and alcohol swabs, such as B-D® Alcohol Swabs, are packaged in this manner.

In another embodiment of the invention, α-MSH, and/or its derivatives, may be administered parenterally. For this embodiment, pharmaceutical preparations of the tripeptide, or its derivatives, may be generally obtained by combining the active ingredient in combination with pharmaceutically acceptable buffers, dilutents, stabilizers, and the like. In a preferred composition, approximately 100 to 500 mg of the active ingredient is dispersed into about 1-7 ml of sterile, isotonic saline, including a pharmacologically accepted buffer to maintain pH at about neutral. Parenteral administration may be desired when a disease manifests a pronounced dermatological involvement, i.e. erythema multiforme.

Additionally, due to its small size, membrane permeability and relatively acid-stable structure, it will be recognized that the α-MSH, and/or its derivatives, may be administered orally, through the oropharanx or nasopharanx via an appropriate inhalant apparatus or anally with the use of a suppository.

Pharmacologically effective concentrations of these peptides may be incorporated into commercial formulations of ointments, creams, gels, parenterals, tablets, or atomized sprays.

Formulations of creams and gels are well known in the art. HARRY'S COMSETICOLOGY (Chemical Publishing, $7^{th}$ ed. 1982); REMINGTON'S PHARMACEUTICAL SCIENCES (Mack Publishing Co., $18^{th}$ ed. 1990).

Set forth below are examples of various formulations of the invention. As used below the term "Active Ingredient" refers to one or more peptides selected from the group of peptides with a C-terminal sequence consisting of KPV, HRFWGKPV and SYSMEHFRWGKPV. Preferably, the active ingredient is KPV or VPK-Ac-CC-Ac-KPV.

An exemplary parenteral preparation comprises:

| Sterile Isotonic Saline | 1–7 cc |
|---|---|
| Pharmaceutically Accepted Buffer | In an amount adequate to maintain pH of about neutral |
| Active Ingredient | 100–500 mg |

An exemplary formulation of a gel based on the invention comprises:

| Propylene Glycol | 100.0 g |
|---|---|
| PEG-Glyceryl Cocoate | 100.0 g |
| di-α-Tocopherol | .2 g |
| Ascorbyl Palmitate | 10 g |
| Propyl Gallate | .02 g |
| Citric Acid, annhydr | .1 g |
| Isopropanol | 500 g |

-continued

| | |
|---|---|
| Hydroxypropyl Methyl Cellulose | 30 g |
| Water | 1000 g |
| Active Ingredient | 8 g–86 g (i.e. 8 g for ½%, 86 g for 5% gel) |

An exemplary formulation of a cream comprises:

| | |
|---|---|
| Glycerol | 50 g |
| Na$_2$-EDTA | .3 g |
| Glycerides | 100 g |
| Cetyl Alcohol | 10 g |
| Stearyl Alcohol | 10 g |
| Glycerol mono Stearate | 40 g |
| Cetereth | 20 g |
| di-α-tocopherol | .2 g |
| Water | 1000.0 g |
| Active Ingredient | 6 g–62 g (i.e. 6 g for ½%; 62 g for 5% cream) |

An exemplary formulation of an absorption base ointment comprises:

| | |
|---|---|
| Cholesterol | 30 g |
| Stearyl Alcohol | 30 g. |
| White Wax | 80 g |
| White Petrolatum | 860 g |
| Active Ingredient | 5–50 g (i.e. 5 g for ½%, 50 g for 5% ointment) |

An example of a water removable ointment comprises:

| | |
|---|---|
| Methylparaben | 0.25 g |
| Propylparaben | 0.15 g |
| Sodium Lauryl Sulfate | 10 g |
| Propylene Glycol | 120 g |
| Stearyl Alcohol | 250 g |
| White Petrolatum | 250 g |
| Purified Water | 370 g |
| Active Ingredient | .5 g–50 g (i.e. .5 g for ½%; 50 g for 5% Ointment |

An exemplary formulation of a hard gelatinous tablet comprise's:

| | |
|---|---|
| Gelatine Bloom 30 | 70.0 mg |
| Maltodextrin MD 05 | 108.0 mg |
| di-α-tocopherol | 2.0 mg |
| Sodium ascorbate | 10.0 mg |
| Microcrystalline cellulose | 48.0 mg |
| Magneisum stearate | 2.0 mg |
| Active Ingredient | $.2 * 10^{-9} - .2 * 10^{-13}$ mg |

An exemplary formulation of a hard tablet comprises:

| | |
|---|---|
| Annhydrous lactose | 130.5 mg |
| Microcrystalline cellulose | 80.0 mg |
| di-α-tocopherol | 2.0 mg |
| Sodium ascorbate | 10.0 mg |
| Polyvinylpyrrolidone K30 | 5.0 mg |
| Magnesium stearate | 2.0 mg |
| Active Ingredient | $.2 * 10^{-9} - .2 * 10^{-13}$ mg |

As mentioned, topical administration may be made with manual application of creams, ointments, gels, or with an atomized spray. Systemic administration may be made by ingestion of hard tablets, soft tablets or capsules or by parenteral administration.

In one preferred embodiment of the invention a therapeutically effective amount αMSH and/or its derivatives is used in combination with an anti-inflammatory agent selected from the group consisting of beclomethasone diprorionate, betamethasone, cortisone, dexamethasone, flucionide, hydrocortisone, methylprednisolone, prednisolone, prednisone, and triamcinolone. The forgoing glucocorticoids may be exchanged in another preferred embodiment of the invention for non-steroidal anti-inflammatory agents selected from the group consisting of aspirin, diflusinal, fenoprophen calcium, ibuprofen, indomethacin, meclofenamate sodium, naproxen, phenylbutazone, piroxicam, sulindac, and tolmetin sodium.

In yet another preferred embodiment of the invention these peptides are used in combination with a therapeutically effective amount of a fungicide selected from the group consisting of: itraconazole, econazole, ketoconazole, miconazole and fluconazole. In yet another preferred embodiment of the invention these peptides are used in combination with a therapeutically effective amount of a gram positive or gram negative antibiotics selected from the group consisting of: aminglycosides, amoxicillin, ampicillin, azithromycin, erythromycin, nafcillin, penecillin, quinupuristin dalfopristin and vancomycin.

The following examples demonstrate the application of α-MSH and its derivatives to treat dermatological disorders.

EXAMPLE I

KPV Equivalents

This example illustrates the biological functional equivalents of α-MSH and/or its derivatives. Although specific amino acid sequences described here are effective, it is clear to those familiar with the art that amino acids can be substituted or deleted without altering the effectiveness of the peptides. Further, it is known that stabilization of the α-MSH and/or its derivatives' sequence can greatly increase the activity of the peptide and that substitution of D-amino acid forms for L-forms can improve or decrease the effectiveness of the peptides. For example, a stable analog of α-MSH, [Nle$^4$,D-Phe$^7$]-α-MSH, which is known to have marked biological activity on melanocytes and melanoma cells, is approximately ten times more potent than the parent peptide in reducing fever. Further, adding amino acids to the C-terminal of α-MSH(11-13) (SEQ. ID. NO. 1) sequence can reduce or enhance antipyretic potency. Addition of glycine to form the 10-13 sequence (SEQ. ID. NO. 5), slightly decreased potency; the 9-13 sequence (SEQ. ID. NO. 6) was almost devoid of activity, whereas the potency of the 8-13 sequence (SEQ. ID. NO. 7) was greater than that of the 11-13 sequence (SEQ. ID. NO. 1). It is known that Ac-[D-K11]-α-MSH 11-13-NH2 has the same general potency as the L-form of the tripeptide α-MSH (11-13) (SEQ. ID. NO. 1). However, substitution with D-proline in position 12 of the tripeptide rendered it inactive. see e.g.

Holdeman, M., et. al., *Antipyretic Activity of a Potent α-MSH Analog*, Peptides 6, 273-5 (1985). Deeter, L. B., et. al., *Antipyretic Properties of Centrally Administered α-MSH Fragments in the Rabbit*, Peptides 9, 1285-8 (1989). Hiltz, M. E., *Anti-inflammatory Activity of α-MSH (11-13) Analogs: Influences of Alterations in Stereochemistry*, Peptides 12, 767-71 (1991).

Biological functional equivalents can also be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid. See, U.S. Pat. No. 5,157,023 issued to James M. Lipton issued on Oct. 20, 1992.

Furthermore, these modified analogs of α-MSH and/or its derivatives can also form dimers as exemplified by the KPV dimer in FIG. 1.

EXAMPLE II

Use of KPV in Treatment of Psoriasis

In a subject with a diagnosed and confirmed greater than ten year history of dermatologically symptomatic psoriasis, KPV was used to treat inflammation, scaling, dryness, pain, erythema, and pruritus. The subject had psoriatic lesions located bilaterally on the volar (palm side) surface of the forearms. The lesions varied in time of existence for greater than ten years with variagated presentation. The subject presented no opportunistic infection of the integument secondary to the psoriatic lesions.

KPV in a crystalline form was prepared as disclosed in U.S. Pat. No. 5,028,592. Mineral oil was chosen as a carrier for the KPV preparation. One milligram of KPV was administered topically on the affected areas of the integument at a frequency of twice daily. For comparison purposes, a standard dosage amount of Hydrocortisone was placed on the contralateral area of the body of the subject that also manifested the dermatological sequelae of psoriasis. Topical administration was accomplished with standard cotton tipped applicators.

Symptoms associated with the psoriatic lesions showed marked improvement within minutes of administration. Similarly, the side treated with Hydrocortisone showed improvement. The lesions treated with Hydrocortisone controlled symptoms for a period of three hours whereas the KPV treated side showed a relief from symptoms for at least eight hours. Symptoms remained limited with KPV applications every day.

This treatment was continued for eleven days. No adverse reactions or side effects were witnessed with the KPV treated side. However, the contralaterally treated Hydrocortisone side showed telangictasia and atrophy of skin, which are known in the art to be associated with continued topical steroid use.

This example shows that the simple topical application of KPV in an appropriate vehicle or carrier has a therapeutic effect on psoriatic lesions that is similar in efficaciousness to an accepted standby treatment; steroid treatment. But KPV is free of many of the unwanted side effects of steroid treatment. This means that one could use KPV for an extended period of time without risking the unwanted complications of long term steroid therapy. One significant advantage is the elimination of the role topical steroids play in secondary infection of the skin.

As mentioned above, psoriasis may create open lesions as well as those typically associated with an outbreak. Opportunistic skin pathogens, *Staphylococcus Aureus*, *Pityrosporon* sp. or *Tricophyton rubrum*, may secondarily infect these open lesions. It is well known that steroid therapy has a tendency to "mask infection" by suppressing the host response to infection. Although the suppression of the inflammatory response is desirable for the reduction of pain, edema and erythema, the inflammatory response is integral to the host defense mechanism against infection. Steroids used alone may ameliorate the symptoms associated with inflammation but may allow an infection to go unnoticed and to become serious and, in systemic infection, be life threatening. KPV has been show to have both antibacterial and antifungal properties and therefore does not present the same risk of masking an infection.

EXAMPLE III

Use of KPV in Contact Dermatitis

This example illustrates the use of KPV in a subject suffering from a type of dermatitis within the class of Eczematous Dermatitis. This type, contact dermatitis, appeared to be the result of contact with leather from a watchband, i.e. leather, was the primary irritant. The subject had been using the particular watchband for 8 months and had noticed a type of rash and pruritus that had developed six months after repeated exposure to the watchband and had continued to worsen with use of the watchband.

Clinically, the subject presented with poorly outlined patches of erythema that included closely grouped vesicles and evidence of excoriation, all of which are indicative of an acute presentation of this type of delayed hypersensitivity reaction. There was no evidence of secondary infection of open wounds or cellulitis.

The subject was given a preparation of KPV as described above in Example I. Marked improvement was noted within minutes of treatment and symptoms did not return.

Contact dermatitis in its acute, subacute and chronic types can lead to secondary infection. As mentioned above, while topical steroids may alleviate the symptoms associated with contact dermatitis, they may also mask a possible infection. Thus, α-MSH and/or its derivatives preparations, have uses and advantages over and above current methods.

The preceding examples demonstrate the application of α-MSH and/or its derivatives for dermatological uses in both treatment and prevention. These are only examples and are not intended to limit the invention to these examples. It is understood that modifying the examples above does not depart from the spirit of the invention. It is further understood that the examples can be applied on their own or in combination with each other. Although the examples above include uses in psoriasis and delayed hypersensitivity reactions, many other dermatological disorders share the same sequelae as those disclosed. For example, atopic dermatitis, also within the class of eczematous dermatitis, presents with scaling, pruritis and a vesicular-type rash. Similarly, seborrheic dermatitis presents with symptoms very much like most of the psoriatic disorders.

What is claimed is:

1. A pharmaceutical composition comprising:
   a) a therapeutically effective amount of a peptide selected from the group consisting of a KPV (SEQ ID NO: 1) polypeptide and the KPV dimer;
   b) a therapeutically effective amount of an non-steroidal anti-inflammatory agent; and
   c) wherein the pharmaceutical composition is used for contact dermatitis.

2. The pharmaceutical composition of claim 1 wherein the non-steroidal anti-inflammatory drug is selected from the group consisting of aspirin, diflusinal, fenoprophen calcium, ibuprophen, indomethacin, meclofenamate sodium, naproxen, phenylbutazone, piroxicam, sulindac, and tolmetin sodium.

3. The pharmaceutical composition of claim 2 further comprising a carrier.

4. The pharmaceutical composition of claim 3 wherein the carrier is selected from the group consisting a cream, an ointment, a balm, a foam, a gel, a stick, and a liquid.

5. The pharmaceutical composition of claim 4 wherein the carrier has its own medicinal properties.

6. The pharmaceutical composition of claim 5 wherein the medicinal properties are selected from the group consisting of emollient properties, analgesic properties, antipruritic properties, and soothing properties or combinations thereof.

7. The pharmaceutical composition of claim 1 wherein the polypeptide is at a concentration of at least $0.2 \times 10^{-9}$ mg.

8. The pharmaceutical composition of claim 7 wherein the polypeptide is at a concentration of at least $0.2 \times 10^{-13}$ mg.

9. A pharmaceutical composition comprising:
   a) a therapeutically effective amount of a peptide selected from the group consisting of a KPV (SEQ ID NO: 1) polypeptide and the KPV dimer;
   b) a therapeutically effective amount of an non-steroidal anti-inflammatory agent; and
   c) wherein the pharmaceutical composition is used for psoriasis.

10. The pharmaceutical composition of claim 9 wherein the non-steroidal anti-inflammatory drug is selected from the group consisting of aspirin, diflusinal, fenoprophen calcium, ibuprophen, indomethacin, meclofenamate sodium, naproxen, phenylbutazone, piroxicam, sulindac, and tolmetin sodium.

11. The pharmaceutical composition of claim 10 further comprising a carrier.

12. The pharmaceutical composition of claim 11 wherein the carrier is selected from the group consisting a cream, an ointment, a balm, a foam, a gel, a stick, and a liquid.

13. The pharmaceutical composition of claim 12 wherein the carrier has its own medicinal properties.

14. The pharmaceutical composition of claim 13 wherein the medicinal properties are selected from the group consisting of emollient properties, analgesic properties, antipruritic properties, and soothing properties or combinations thereof.

15. The pharmaceutical composition of claim 9 wherein the polypeptide is at a concentration of at least $0.2 \times 10^{-9}$ mg.

16. The pharmaceutical composition of claim 15 wherein the polypeptide is at a concentration of at least $0.2 \times 10^{-13}$ mg.

* * * * *